(12) United States Patent
Kohler

(10) Patent No.: US 9,566,104 B2
(45) Date of Patent: Feb. 14, 2017

(54) REDUCTION FORCEPS WITH DUAL 90°-DEFORMATION FOR DISTRIBUTION AMONG TWO PLANES

(71) Applicant: Karl Leibinger Medizintechnik GmbH & Co. KG, Donau (DE)

(72) Inventor: Klaus Kohler, Hausen (DE)

(73) Assignee: Karl Leibinger Medizintechnik GmbH & Co. KG, Muehlheim a.d. Donau (DE)

( * ) Notice: Subject to any disclaimer, the term of this patent is extended or adjusted under 35 U.S.C. 154(b) by 161 days.

(21) Appl. No.: 14/482,913

(22) Filed: Sep. 10, 2014

(65) Prior Publication Data

US 2015/0100080 A1   Apr. 9, 2015

(30) Foreign Application Priority Data

Oct. 8, 2013   (EP) .................................... 13187700

(51) Int. Cl.
*A61B 17/00*   (2006.01)
*A61B 17/88*   (2006.01)
(Continued)

(52) U.S. Cl.
CPC ......... *A61B 17/8866* (2013.01); *A61B 17/282* (2013.01); *A61B 17/808* (2013.01);
(Continued)

(58) Field of Classification Search
CPC ... A61B 17/28; A61B 17/2812; A61B 17/282; A61B 17/29; A61B 17/808; A61B 17/8866; A61B 2017/2808; A61B 2017/2901;A61B 2017/291; A61B 2017/2926; A61M 25/02; A61M 2025/024
See application file for complete search history.

(56) References Cited

U.S. PATENT DOCUMENTS 4,611,592 A * 9/1986 Talboy ................. A61B 17/282
128/852
5,059,198 A   10/1991 Gimpelson
(Continued)

FOREIGN PATENT DOCUMENTS

CN   201806774   4/2011
CN   202515727   11/2012
(Continued)

OTHER PUBLICATIONS

European Search Report dated Mar. 27, 2014 from European Application No. EP 13 187 700.3.

*Primary Examiner* — Robert Lynch
(74) *Attorney, Agent, or Firm* — Beyer Law Group LLP

(57) ABSTRACT

The invention relates to a reduction forceps comprising a first rod and a second rod, which are supported on a swivel joint defining an axis of rotation such that they are pivotable relative to one another, the first rod comprising on one side of the swivel joint a first jaw and the second rod comprising, on the same side of the swivel joint, a second jaw provided for cooperation with the first jaw, both said jaws having defined thereon contact points for contacting a bone or a bone plate, said contact points being movable in a common pivoting plane, which comprises the swivel joint and in which the axis of rotation extends perpendicularly, and at least one of the jaws being sectionwise displaced in the direction of a plane extending parallel to the pivoting plane.

15 Claims, 5 Drawing Sheets

Figure 5:
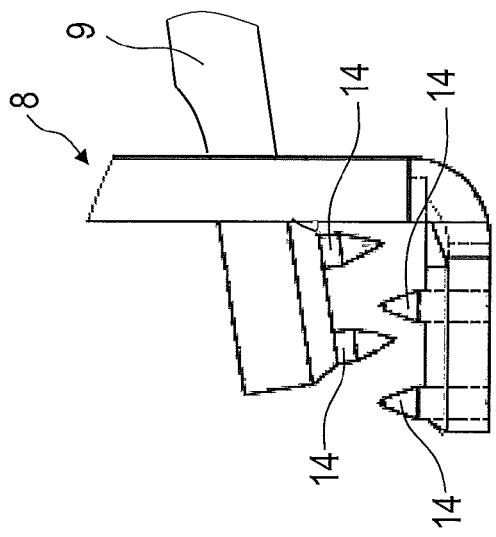

(51) Int. Cl.
*A61B 17/28* (2006.01)
*A61B 17/80* (2006.01)
A61M 25/02 (2006.01)
A61B 17/29 (2006.01)

(52) U.S. Cl.
CPC .......... *A61B 17/28* (2013.01); *A61B 17/2812* (2013.01); *A61B 17/29* (2013.01); *A61B 17/8863* (2013.01); *A61B 2017/2808* (2013.01); *A61B 2017/2837* (2013.01); *A61B 2017/291* (2013.01); *A61B 2017/2901* (2013.01); *A61B 2017/2926* (2013.01); *A61M 25/02* (2013.01); *A61M 2025/024* (2013.01)

(56) References Cited

U.S. PATENT DOCUMENTS

2004/0006371 A1 1/2004 Choi
2013/0144313 A1 6/2013 Hahn et al.

FOREIGN PATENT DOCUMENTS

| | | |
|---|---|---|
| DE | 83 23 877 | 1/1984 |
| DE | 86 12 466.8 | 6/1986 |
| DE | 87 02 813.1 | 5/1987 |
| DE | 101 96 657 | 7/2007 |
| EP | 1 811 909 | 2/2011 |
| WO | 02/24124 | 3/2002 |
| WO | 2006/049960 | 5/2006 |
| WO | 2010/014719 | 2/2010 |

* cited by examiner

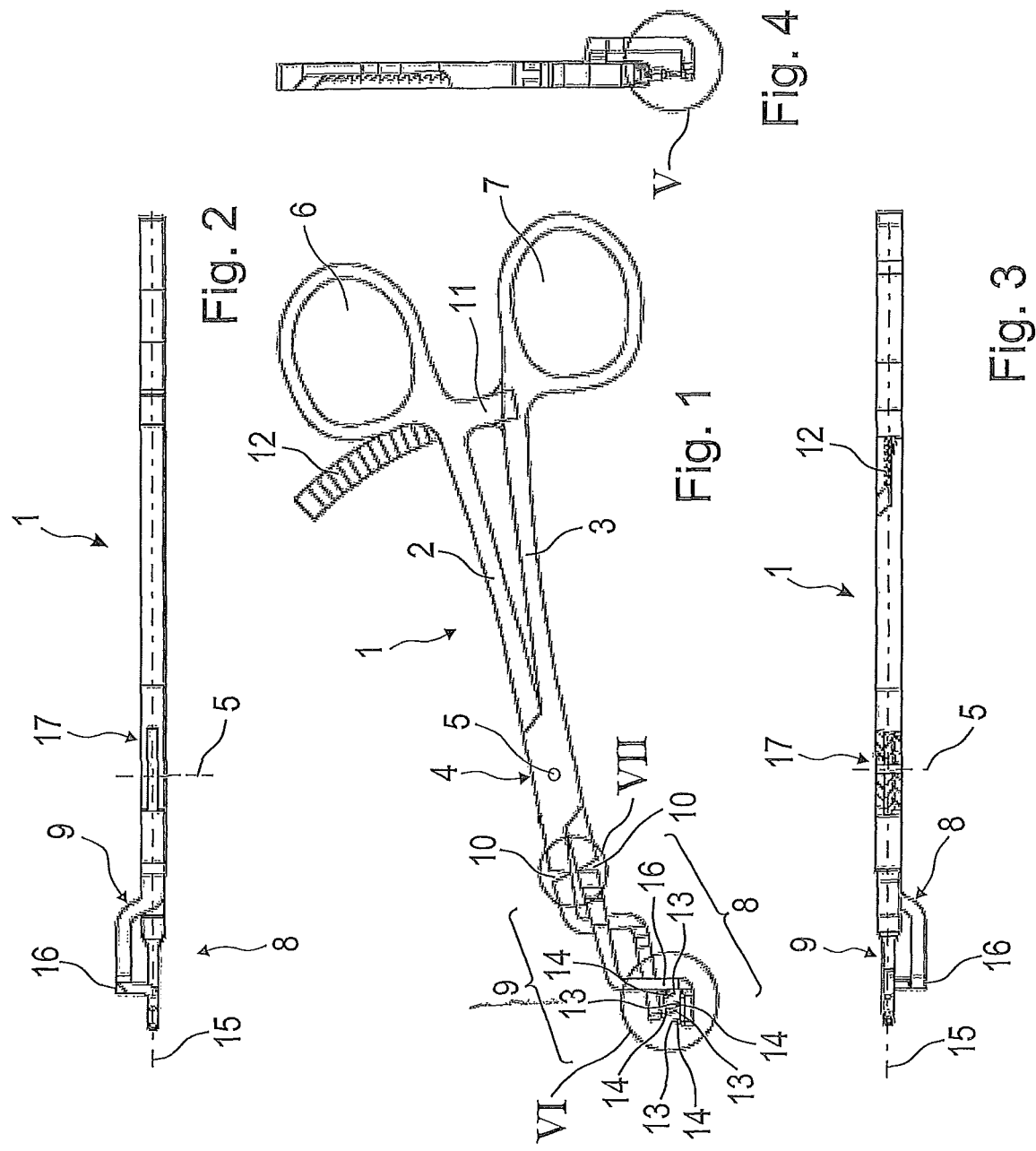

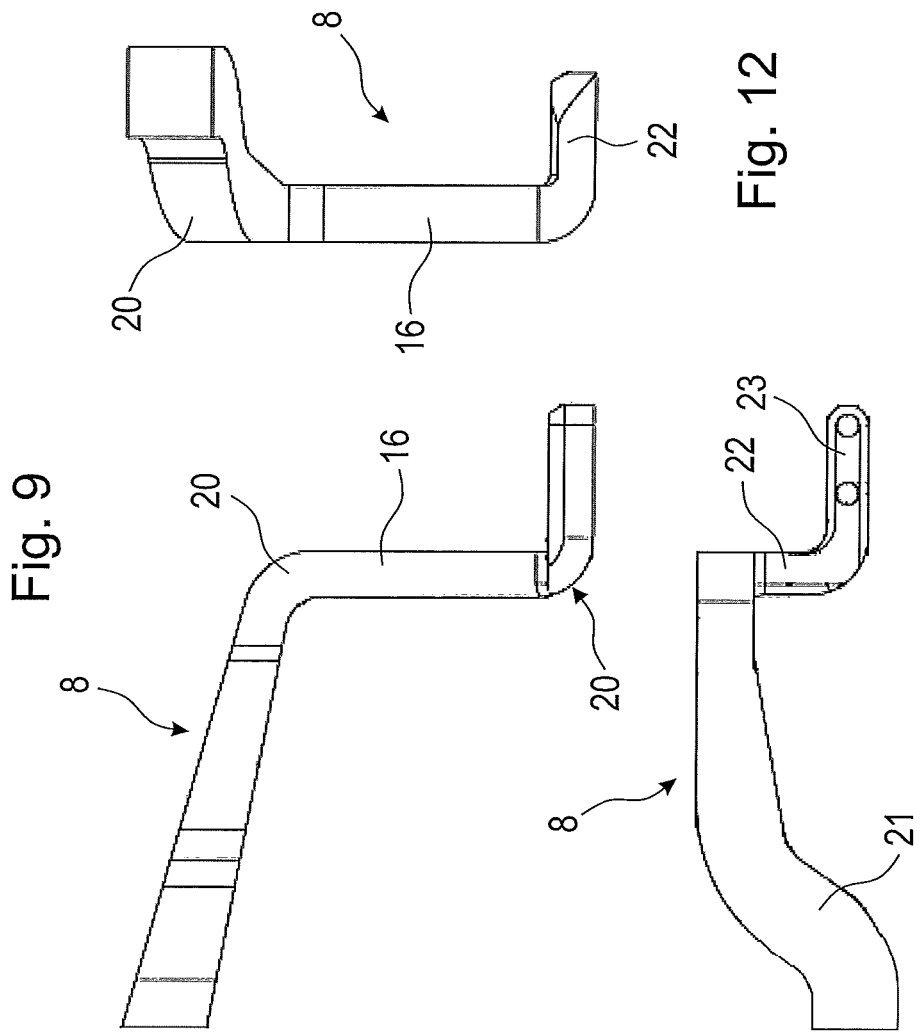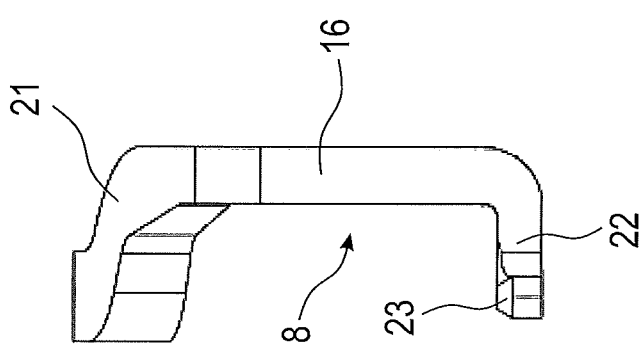

REDUCTION FORCEPS WITH DUAL 90°-DEFORMATION FOR DISTRIBUTION AMONG TWO PLANES

FIELD OF THE INVENTION

The present invention relates to a reduction forceps comprising a first rod and a second rod, which are supported on a swivel joint defining an axis of rotation such that they are pivotable or rotatable relative to one another, the first rod comprising on one side of the swivel joint a first jaw, such as a first branch, and the second rod comprising on the same side of the swivel joint a second jaw, such as a second branch, provided for cooperation with the first jaw, both said jaws having defined thereon contact points for contacting a bone or a bone plate.

The prior art, e.g. US 2004/0006371 A1, WO 2006/049960 A1, US 2013/0144313 A1, U.S. Pat. No. 5,059,198 A, DE 87 02 813 U1 or DE 86 12 466 U1, already discloses similar surgical forceps. DE 101 96 657 B4 discloses a forceps for engagement with a mandibular angle on both sides of a fracture, said forceps consisting of a first member and a second member, which are combined with each other at a joint and which comprise grips on one side of each element and, on the other side of said element, linear portions proximal to the joint and curved portions which extend from the front ends of the linear portions and which have tips, a special characteristic being that the curved portion of the first element has the tip that points in a direction parallel to the axis of the joint and the curved portion of the second element has a tip and an extension part.

EP 1 811 909 B1 discloses an intravaginal device for treating a uterine disorder of a female patient by occluding at least one of the patient's uterine arteries. The device comprises a first clamping member and a second clamping member, the first clamping member having an elongated handle with a proximal handle portion, which is configured to extend out of the patient during treatment and be manipulated by an operator, and with a distal handle portion having a pivot point and configured to rotate in a plane about the pivot point, and further comprises an open, paddle-shaped jaw, which is secured to the distal handle portion, which has a distal tip with a pressure applying surface, and which has a tissue receiving recess proximal to the pressure applying surface, a pair of longitudinally oriented sides, which are located proximal to the distal tip, defining in part the tissue receiving recess, a first longitudinally oriented side being in line with the distal handle portion and a second longitudinally oriented side being spaced apart from said first longitudinally oriented side.

Also CN 201806774 U1 discloses a forceps for use on a bone.

A similar forceps is also known from CN 202515727 U.

A reduction forceps is additionally known from DE 83 23 877 U1, said reduction forceps comprising two forceps branches, which are fixedly centered or adapted to be combined so as to form a self-centering forceps and which are adapted to be released without making use of a tool, the jaws of both forceps branches being differently sized and differently shaped.

A reduction forceps for contacting a bone plate and a method of using the same are also known from WO 2010/014719 A1.

However, the hitherto known reduction forceps project too far from the bone at many positions during bone repositioning processes. This may lead to injuries of the soft tissue, since said tissue has to be pushed away. When more space is to be provided for the reduction forceps, more soft tissue must be dissected and/or removed from the bone. This will increase the size of the wound. In addition, the applicability of hitherto known forceps is limited at different positions or not given at all.

In other words, the hitherto known reduction forceps are shaped such that they take up too much space so that soft tissue will be injured during minimum dissection processes or that, in order to avoid this, tissue has to be dissected from the bone on larger areas thereof.

It is therefore the object of the present invention to avoid the drawbacks entailed by the prior art and to provide a durable, reasonably priced reduction forceps that is versatile and precise in use.

According to the present invention, this object is achieved in that the contact points are movable in a common pivoting plane, which comprises the swivel joint and in which the axis of rotation extends perpendicularly, and at least one of the jaws or branches is sectionwise displaced in the direction of a plane extending parallel to the pivoting plane, e.g. a parallel plane.

Such a reduction forceps adapts itself better to the contour of the bone. This improved adaptation is also accomplished when a change of angles takes place in the forceps.

Thus, a lower jaw of the forceps that is angled more than once is provided. In principle, the lower jaw is offset by approx. 90°, the 90° offset being distributed among two planes through a connection piece.

Advantageous embodiments are claimed in the subclaims and will be explained in more detail hereinbelow.

It will e.g. be advantageous when only one of the two jaws is oriented in the direction of the plane that extends parallel to the pivoting plane, i.e. the parallel plane. The other of the two jaws, e.g. the second rod with the second jaw, is then configured straight or at least arranged in a working plane which takes up the longitudinal axis of the second rod and/or of the second jaw and which may be congruent with the pivoting plane. The production of such a reduction forceps half is then particularly cost-effective.

It goes without saying that also both jaws may move away from and return to the pivoting plane.

It will also be of advantage when a preferably straight section is arranged such that it extends in the plane that is parallel to the pivoting plane. The straight section is then a component part of the respective jaw, e.g. of the first jaw.

It may be of advantage when the end areas, i.e. the areas of the free ends of the two jaws, are oriented parallel to one another and above/below one another in alignment.

An advantageous embodiment is also characterized in that the first jaw is configured as a lower branch and the second jaw is configured as an upper branch, a free end of the lower branch being disposed below the upper branch, when seen in the pivoting plane. The above-mentioned bringing into alignment is then more easily possible.

When the second jaw is arranged fully or at least mainly in the pivoting plane, an occurrence of torques is substantially prevented.

In addition, it will be of advantage when the second jaw includes one, two or more change-of-direction areas in the pivoting plane between the swivel joint and the free end of the second jaw. The change-of-direction areas will then change the orientation of the jaw in a specific plane thus allowing effective gripping of and/or engagement behind the bone to be treated, e.g. a human finger bone.

In order to allow, in the case of a parallel orientation of the reduction forceps relative to the bone, the individual jaw components to be guided along the bone at the least possible distance therefrom, it will be of advantage when, at the change-of-direction area, the second jaw exhibits a change of direction, a bend or a sharp bend of approx. 75° to approx. 115°, preferably approx. 85°, approx. 90° or approx. 95°.

Production can be simplified when the change-of-direction area is created by means of a chip removing process, e.g. milling, or by means of a bending process. A milling variant is here specially preferred.

The dissection of tissue from the bone can be limited to a particularly small area, when the first jaw and/or the second jaw become/becomes narrower, continuously or discontinuously/sectionwise/in steps, from the swivel joint to the respective free end.

When the first jaw includes one, two or more change-of-orientation areas between the swivel joint and the free end of the first jaw in the plane extending parallel to the pivoting plane, minimally invasive surgery on a finger whose bone is to be treated will suffice. The area in which dissection is to be carried out remains small.

It will be of advantage when at the change-of-orientation area the first jaw exhibits a change of direction, a bend or a sharp bend of approx. 75° to approx. 115°, preferably approx. 85°, approx. 90° or approx. 95°.

In this context, it will be advantageous when the change-of-direction area and the change-of-orientation area cause the same change of orientation/change of direction/deflection on the respective jaw. In the final analysis, the two jaws may be configured such that they are, at least in certain sections thereof, symmetrical or even identical.

An advantageous embodiment is also characterized in that the first jaw comprises a connection piece proximal to the end and/or a connection piece proximal to the swivel joint. The two connection pieces then connect the pivoting plane to the parallel plane.

In this respect it will be of advantage when the connection piece is oriented transversely to the pivoting plane. The term "transversely" herein includes an orientation orthogonal to the pivoting plane as well as an orientation crosswise to the pivoting plane, crossing by an angle smaller (or larger) than 90°. Preferably, the connection piece is oriented substantially orthogonal thereto or at an angle of approx. 45°. It will here be advantageous when the connection piece proximal to the end exhibits an angle of 90° relative to the nearest jaw portion and when the connection piece proximal to the swivel joint exhibits an angle of approx. 45° to the respective nearest jaw portion.

Production can be simplified when two of the change-of-orientation areas and/or at least the section disposed therebetween are arranged fully in the plane parallel to the pivoting plane, i.e. the parallel plane.

In addition, it will be of advantage when the connection piece located proximal to the end is followed on the end side thereof by an end part, which is preferably located fully in the pivoting plane that is common to the two jaws.

It will be of advantage when the first jaw and/or the second jaw have provided thereon at least one holding element projecting from the respective jaw orthogonally thereto and directed/oriented towards the respective other jaw.

As a further development of the above concept, it will be of advantage when a jaw, e.g. the first jaw, has arranged thereon two successive holding elements in the pivoting plane, when seen from the swivel joint.

The holding element may be configured as a peg, spine, pin or stud and it may preferably be shaped like a cone, at least at the free end thereof.

When the reduction forceps has installed therein four pins, two at the top and two at the bottom, improved anchoring of the reduction forceps on the bone will be guaranteed. When the pins are configured for penetrating into the bone, without having to overcome major resistance, the anchoring will be improved still further. The reduction forceps will be prevented from slipping off from the bone and a more stable position of the bone will be guaranteed.

It will be of advantage when the first rod is arranged side by side with the second rod in the area of the swivel joint, i.e. when the two rods are located in different planes that are parallel to one another, or when the two rods are in contact with one another via a box lock. A box lock is a type of connection in the case of which one rod is surrounded on both sides thereof by subareas of the other rod, i.e. is passed through the other rod.

It will be of advantage when the first jaw exhibits one or two changes of orientation/bends or when it exhibits a change of direction or is bent at least about two change-of-orientation axes/bending axes that are orthogonal relative to each other.

In this respect it will be of advantage when the planes in which the two change-of-orientation axes/bending axes extend are spaced apart substantially at a distance corresponding to one third to two thirds, preferably to half the width of a bone to be treated, measured transversely to the longitudinal direction thereof.

It will be expedient when the swivel joint comprises a cylindrical bearing element, such as a pin, a journal or a screw, defining the axis of rotation.

The use of known handle portions, e.g. with catch mechanisms or locking mechanisms, will be advantageous when the first rod and/or the second rod exhibit a weld seam between the swivel joint and the free end of the jaw. The weld seam may also be provided on the swivel joint side facing away from the jaw. The weld seam may have been produced by means of MIG, MAG or WIG processes.

As regards the durability, it will be of advantage when the first jaw is configured as a one-piece integral component.

In this context, it is also of advantage when the second jaw is configured as a one-piece integral component. These two subforms also simplify the production process.

When the length of the jaws from the axis of rotation to the respective free end of the jaws and the length of the holding element/holding elements are adapted for gripping a cylinder having a thickness of 4 mm to 14 mm, bone repositioning can be used efficiently.

The bone-holding reliability can be improved by configuring the ends of the two jaws as a four-point support for holding a bone.

It should not be left unmentioned that it is of advantage that the first or second jaw is composed of a sequence of different, straight portions without exhibiting a continuous bend in three dimensions. The present invention also relates to a method of contacting a bone, e.g. a finger bone, and/or a bone connecting plate with a reduction forceps according to the present invention. The method may replace preoperative planning. In addition to the taking of standard pictures at the neutral position of e.g. a hand to be treated in the anterior-posterior as well as lateral ray paths, a high-resolution computer tomography may be executed in the case of intra-articular fractures for further diagnosis.

The patient is placed in the supine position on an operating table. The hand to be operated on is placed in the pronation position of the lower arm on the lateral hand table. Lateral access is provided. Opening is performed via a lateral, straight incision starting on the level of the MCP joint and continuing up to the PIP joint.

In the next step which, just as the preceding and the subsequent steps described, is carried out in precisely this temporal sequence, the representation of the fracture is made possible. After incision of the skin, the radial, ulnar and median nerves are first localized. The obliquely extending fibers of a collateral ligament are retracted by two retractors. The periosteum is only lifted directly adjacent to the fracture so as to prevent scar formation, ligament adhesion and devascularization of the bone fragments.

The next step to be carried out is the reduction of the fracture. In addition to manual reduction of the fracture by the operating surgeon, either a small Backhaus forceps integrated into the Linos system can be used or a reduction forceps specially developed for finger fractures. The reduction forceps then presents all its numerous advantages.

Subsequently, selection and subsequent placement of an osteosynthesis plate takes place. By way of example, treatment in the present indication is performed using an 0.8 mm T-plate. The osteosynthesis plate is always selected according to the course of the fracture and the patient's anatomy. If necessary, the osteosynthesis plate is adapted to the anatomical situation using two plate bending forceps. The respective plate bending forceps is a special subtype of the reduction forceps, viz. a forceps using on the upper jaw/upper branch a single pin acting as a holding element, said pin being adapted to the inner contour of a hole in the plate.

The plate can temporarily be fixated with 0.9 mm K-wires. Special K-wire holes are provided for this purpose. Alternatively, a Linos plate holding forceps can also be used.

In the next step carried out now, a first core hole is drilled. For ensuring closure of the fracture gap, it will be advisable to choose the sequence of screw implantations such that a compression hole can be used. Hence, the holes remote from the elongated hole are first provided with screws. To this end, the core hole is drilled first with the aid of the drill guide and the appropriate core hole drill. The Linos system makes it possible to use standard and multidirectional locking "smart drive screws" with diameters of 1.5 mm, 2 mm, 2.3 mm in all plate holes.

Subsequently, the screw length is determined. The correct screw length is determined with a depth gauge, which can be used in all cases for screw diameters of 1.5, 2.0 and 2.3 mm A color code is here adapted to the screw diameters. Following this, a first screw is placed. The plate is first fixated with a 2.0 mm standard "smart drive screw". To this end, the screw is picked up and inserted with the respective color-coded screwdriver, which is used for the diameters 1.5 or 2.0 or 2.3 mm Now the second screw is placed by means of the technique described above. Optionally, a multidirectional locking screw can be used to increase stability. Correct positioning of the plate is guaranteed by an X-ray check. Subsequently, the compression screw is placed. After successful implantation of the first screws, the compression screw is now introduced into the elongated hole in order to securely close the fracture gap. Standard screws with diameters of 1.5, 2.0 or 2.3 mm are used. For this purpose, the compression drill sleeve is clicked into the open working end of the drill guide from below. The arrows on the compression drill sleeve then point towards the fracture when drilling. Analogously with the first screw, the core hole is drilled and the length of the screw is determined.

Following this, the fracture gap is closed. When it is being inserted, the "smart drive screw" glides over the inclined plane integrated in the elongated hole towards the fracture gap and closes it.

Subsequently, further screws are placed. To achieve adequate early functional stability more plate holes are filled with screws. The procedure for this corresponds to the above-mentioned steps. The number of screws and the selection of the screw diameter and type depend on the specific anatomy of the patient and the required stability.

Now the wound has to be closed. When the periosteum has been reliably closed, skin suture is performed with a non-absorbable suture material.

Following this, an after-treatment will have to be carried out. After surgery, the treated finger is fixed by means of a bandage so as to neutralize lateral forces acting on the finger.

Normally, the patient will present for a follow-up examination after five and after ten days.

Immediately after surgery, the patient may start functional exercise.

Removing the metal is advisable in particular in the event that soft tissue irritation should occur or that the mobility of the joints and of the finger should be impaired.

The holding elements, such as pins or spines, may be inserted in the otherwise integral jaw, e.g. in holes, as separate components through press-fitting.

It follows that a reduction forceps is presented, which comprises two legs that are pivotably connected to one another by a joint, a respective force application point being definable on a jaw of each leg, said force application point having, when seen exclusively from the point of view of rigid-body mechanics and when an object is gripped by means of the reduction forceps, applied thereto a single resultant force whose effect corresponds to the effect of all the forces acting from the leg onto the object in question, and the two resultant forces of the two legs being identical in magnitude, wherein the force application points are located at different distances from the joint and at least one of said legs extends, at least sectionwise, transversely to a plane defined by the joint and the force application points.

Figure 6:
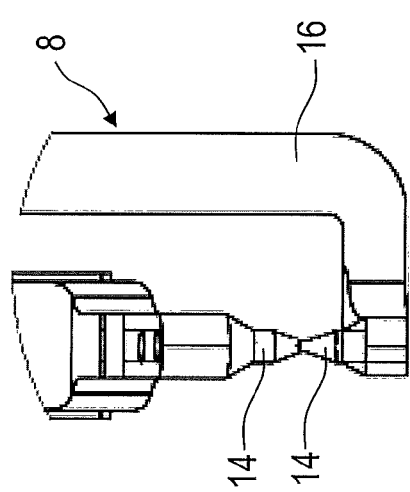
Figure 7:
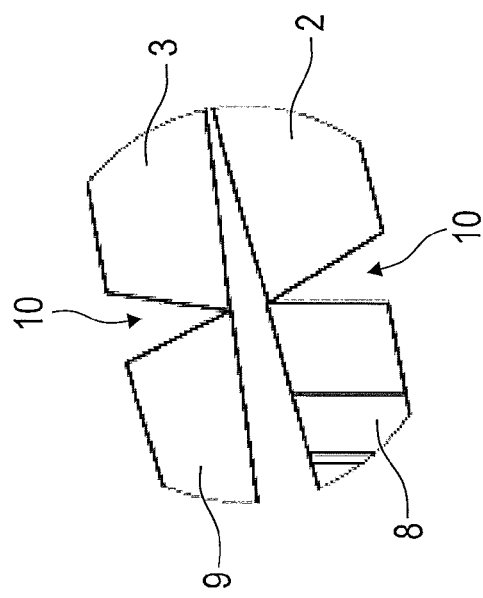
Figure 8:
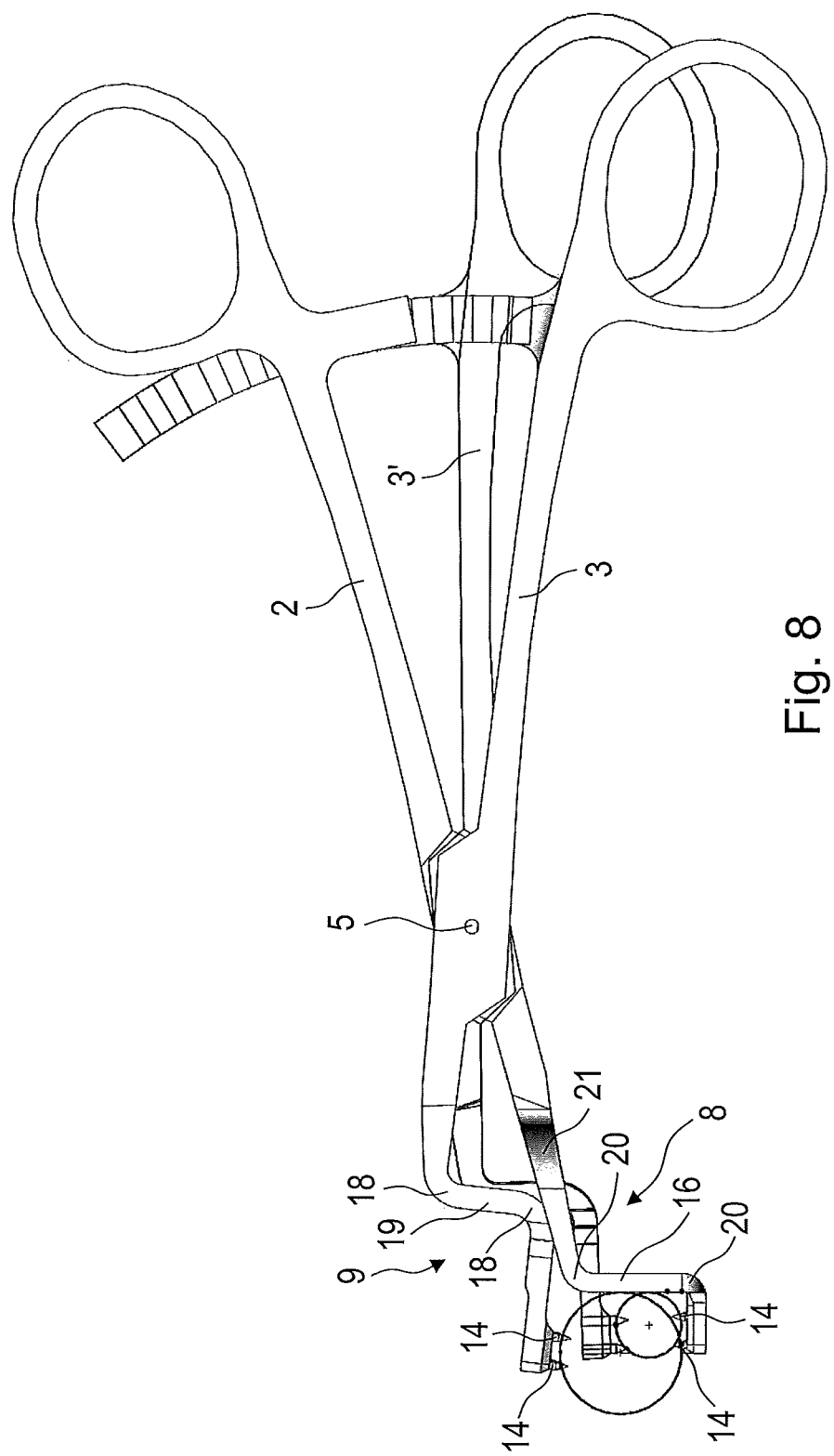
Figure 13:
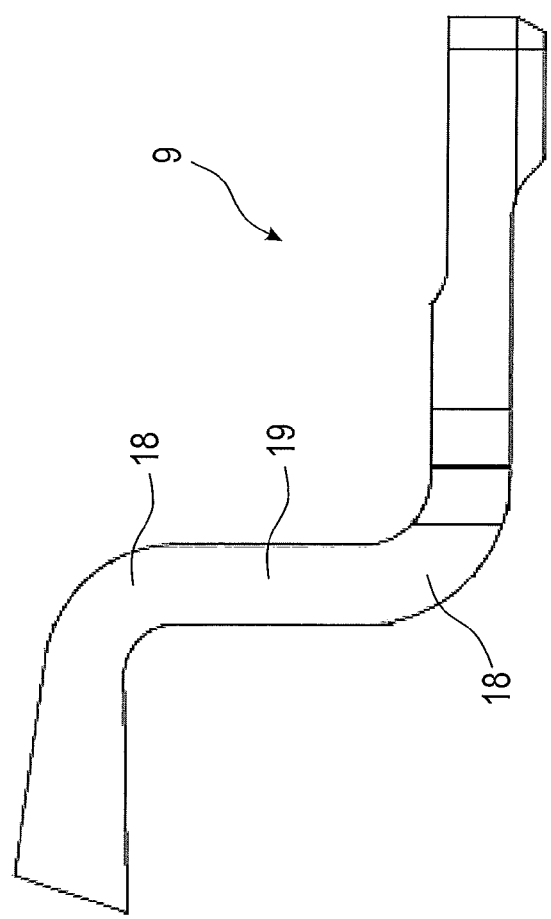
Figure 14:
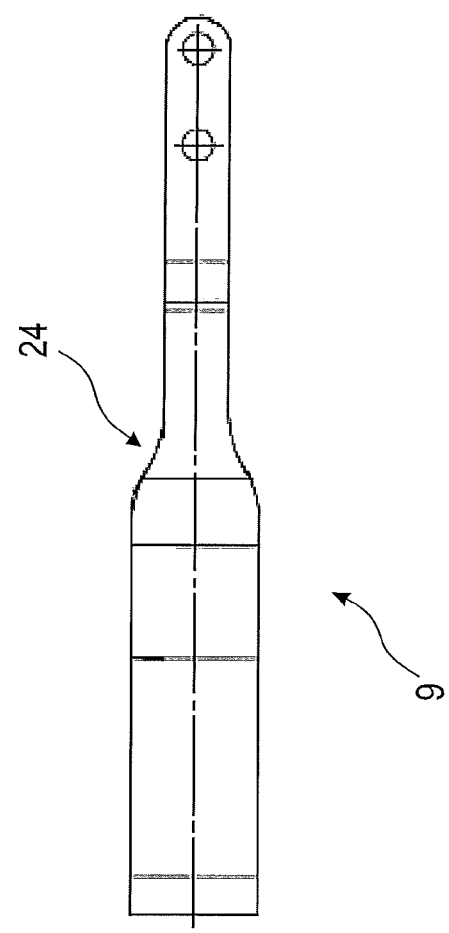

In the following the present invention will be explained in more detail making reference to a drawing, in which a first embodiment is shown and in which:

FIG. 1 shows a side view of a reduction forceps according to a first embodiment, FIG. 2 shows a view from below of the reduction forceps according to FIG. 1, FIG. 3 shows a view of the reduction forceps according to FIG. 1 from above, FIG. 4 shows a front view of the reduction forceps according to FIG. 1, FIG. 5 shows a front view of the closed reduction forceps in the area of the enlarged detail V according to FIG. 4, FIG. 6 shows an enlarged representation of area VI according to FIG. 1, FIG. 7 shows an enlarged representation of area VII of FIG. 1 representing the closed reduction forceps, FIG. 8 shows the reduction forceps according to FIGS. 1 to 7 in a closed and in an intersecting open position, FIG. 9 shows a side view of the first jaw (lower branch/lower jaw), FIG. 10 shows a top view of the first jaw according to FIG. 9, FIG. 11 shows a front view of the first jaw according to FIGS. 9 and 10, FIG. 12 shows a rear view of the first jaw according to FIGS. 9 to 11, FIG. 13 shows a side view of the second jaw (upper jaw/upper branch), and FIG. 14 shows a top view of the second jaw according to FIG. 13.

The figures are only of a schematic nature and they only serve to make the present invention understandable Like elements are designated by like reference numerals. Features which are not represented as being essential are merely optional and are therefore exchangeable.

FIG. 1 shows a reduction forceps 1 according to a first embodiment. The reduction forceps 1 comprises a first rod 2 and a second rod 3. The first rod 2 is connected to the second rod 3 at a swivel joint 4. The swivel joint 4 may also be referred to as swivel, pivot bearing or pivot joint. It comprises an axis of rotation 5, which projects through the two rods 2 and 3 perpendicular thereto and which is defined by a stud. The first rod 2 has, on one end thereof, a handle 6 for accommodating a finger of an operator, and also the second rod 3 has, on the same side, a handle 7 for accommodating another finger of the operator.

The first rod 2 has, on the other end thereof, i.e. on the end opposite the handle 6, a first jaw 8. The second rod 3 has, on the same side of the axis of rotation 5, a second jaw 9. On the swivel-joint-side end of the two jaws 8 and 9, a notch 10 is provided for accommodating a weld seam, which is here not shown. The notch 10 is shown in a particularly clear manner in FIG. 7.

Referring once more to FIG. 1, it should be explained that the first jaw 8 defines the lower jaw, i.e. the lower branch. The second jaw 9 defines the upper branch, i.e. the upper jaw. It is clearly visible that the handle 6 has provided thereon a projection 11, which is adapted to be brought into operative contact with a detent/locking/catch mechanism 12.

FIG. 3 shows clearly that contact points 13 in the vicinity of the free ends of the two jaws 8 and 9, viz. contact points 13 created by the tips of holding elements 14, are movable in a common pivoting plane, in which a pivot point determined by the axis of rotation 5 is located, the axis of rotation 5 extending perpendicular in this defined pivoting plane. Also the longitudinal axis 15 of the reduction forceps 1, which also defines the longitudinal axis of the second rod 3, is embedded in said pivoting plane.

A straight section 16 is fully embedded in a plane extending parallel to the pivoting plane, i.e. a parallel plane. The two planes are spaced apart by a distance between 6 and 10 mm, preferably 7.5 mm.

In FIGS. 2 and 3 a box lock 17 used for connecting the two rods 2 and 3 is indicated. The whole reduction forceps 1 has a length in the range of 140 to 145 mm.

The first jaw 8 moves away from the pivoting plane into the parallel plane and back into the pivoting plane. The contact points 13 are arranged almost one on top of the other or are at least located in the same pivoting plane.

The holding elements 14 are configured as spines. This is also clearly shown in FIGS. 5 and 6.

The holding elements 14 may be press-fitted and/or welded into the respective jaw 8 or 9. The two jaws 8 and 9 are hardened, preferably hardened with 46+/−2 HRC. FIG. 8 shows clearly that the center of a cylinder, which is almost 2.5 times as large and which is adapted to be gripped by the reduction forceps 1, moves further away from the axis of rotation 5 by 10%. The rod 3 moves to the position 3' when the forceps is being closed. The second jaw 9 exhibits two changes of direction of angles of approx. 89° measured on the lower side and angles of approx. 98° measured on the upper side at the location of a change-of-direction area 18. A second change-of-direction area 18 arranged further down and more distally exhibits an angle of approx. 90° with an inner radius of approx. 2 mm and an outer radius of approx. 5 mm A non-curved straight part 19 extends therebetween.

The first jaw 8 exhibits two change-of-orientation areas 20. The straight section 16 is located therebetween in the parallel plane. A connection piece 21, which is proximal to the swivel joint, follows on the swivel-joint side of the change-of-orientation area 20 that is more proximal to the swivel joint.

The change-of-orientation area 20 of the two change-of-orientation areas 20 that is more proximal to the end is followed by a connection piece 22 proximal to the end. When the person skilled in the art takes into account FIGS. 9 and 10 in combination, he is presented with a three-dimensional picture, which is additionally supported by FIGS. 11 and 12.

The connection piece 22 proximal to the end is followed by an end part 23. On the basis of FIG. 10 it is easily imaginable that, in the connection area, an angle of approx. 135° and approx. 125°, respectively, is defined between the connection piece 21 proximal to the swivel joint and the leg portions extending there.

FIGS. 13 and 14 show the second jaw 9 in more detail, a section of reduced diameter 24 being there provided. The holding elements 14 are not contained in the representations according to FIGS. 9 to 14.

The invention claimed is:

1. A reduction forceps comprising a first rod and a second rod, which are supported on a swivel joint defining an axis of rotation such that the first and second rods are pivotable relative to one another, the first rod comprising on one side of the swivel joint a first jaw and the second rod comprising, on the same side of the swivel joint, a second jaw provided for cooperation with the first jaw, both said jaws having defined thereon contact points prepared for contacting a bone or a bone plate, wherein:
   the contact points are movable in a common pivoting plane, which comprises the swivel joint and in which the axis of rotation extends perpendicularly; and
   a first one of the jaws has a section that is displaced from the pivoting plane and extends in a plane extending parallel to the pivoting plane and includes a curved portion formed in the plane extending parallel to the pivoting plane; and
   a second one of the jaws includes a S-curved portion, which is formed in the pivoting plane.

2. The reduction forceps according to claim 1, characterized in that only one of the two jaws is oriented in the direction of the plane that is parallel to the pivoting plane.

3. The reduction forceps according to claim 1, characterized in that the first jaw is configured as a lower branch and the second jaw is configured as an upper branch, a free end of the lower branch being disposed below the upper branch, when seen in the pivoting plane.

4. The reduction forceps according to claim 1, characterized in that the second jaw is arranged fully or mainly in the pivoting plane.

5. The reduction forceps according to claim 1, characterized in that the second jaw includes one, two or more change-of-direction areas in the pivoting plane between the swivel joint and the free end of the second jaw.

6. The reduction forceps according to claim 5, characterized in that at the change-of-direction area the second jaw exhibits a change of direction, a bend or a sharp bend of approx. 75° to approx. 115°.

7. The reduction forceps according to claim 6, characterized in that:

the first jaw includes one or more change-of-orientation areas between the swivel joint and the free end of the first jaw in the plane extending parallel to the pivoting plane; and the change-of-direction area and the change-of-orientation area cause the same change of orientation in the respective jaws.

8. The reduction forceps according to claim 5, characterized in that at the change-of-direction area the second jaw exhibits a change of direction, a bend or a sharp bend of approximately 85° to approximately 95°.

9. The reduction forceps according to claim 1, characterized in that the first jaw and/or the second jaw become/becomes narrower, continuously or in steps, from the swivel joint to the respective free end.

10. The reduction forceps according to claim 1, characterized in that the first jaw includes one, two or more change-of-orientation areas between the swivel joint and the free end of the first jaw in the plane extending parallel to the pivoting plane.

11. The reduction forceps according to claim 10, characterized in that at the change-of-orientation area the first jaw exhibits a change of direction, a bend or a sharp bend of approx. 75° to approx. 115°.

12. The reduction forceps according to claim 10, characterized in that two of the change-of-orientation areas and/or at least the section arranged therebetween are arranged fully in the plane extending parallel to the pivoting plane.

13. The reduction forceps according to claim 1, characterized in that the second rod provided with the second jaw is arranged in a working plane, which takes up the longitudinal axis of the second rod and which is congruent with the pivoting plane.

14. The reduction forceps according to claim 13, characterized in that a connection piece is oriented transversely to the pivoting plane, preferably substantially orthogonal thereto or at an angle of approx. 45°.

15. The reduction forceps according to claim 1, characterized in that the curved portion has a bend angle of at least 90° in the plane parallel to the pivoting plane.

\* \* \* \* \*